United States Patent [19]

Munson, Jr. et al.

[11] Patent Number: 5,916,562
[45] Date of Patent: Jun. 29, 1999

[54] MEMBRANE PROTEINS AND PEPTIDES OF HAEMOPHILUS INFLUENZAE TYPE B

[75] Inventors: Robert S. Munson, Jr., Ballwin, Mo.; Robert Tolan, Indianapolis, Ind.; Pele Chong, Richmond Hill; Raafat Fahim, Mississauge, both of Canada; Patrick McVerry, Stroudsburg, Pa.; Michel Klein, Willowdale, Canada

[73] Assignees: Connaught Laboratories Limited, North York, Canada; Washington University, St. Louis

[21] Appl. No.: 08/123,245

[22] Filed: Sep. 20, 1993

Related U.S. Application Data

[63] Continuation of application No. 07/853,015, Mar. 18, 1992, abandoned, which is a continuation of application No. 07/456,000, Dec. 22, 1989, abandoned.

[30] Foreign Application Priority Data

Dec. 23, 1988 [GB] United Kingdom .................. 8830124
Feb. 1, 1989 [GB] United Kingdom .................. 8902178

[51] Int. Cl.⁶ .................................................. A61K 39/02
[52] U.S. Cl. .................. 424/190.1; 435/69.1; 435/172.3
[58] Field of Search ................................. 424/92, 190.1; 530/350, 405; 435/69.1, 7.1, 172.3

[56] References Cited

U.S. PATENT DOCUMENTS 4,762,713  8/1988  Anderson et al. ......................... 424/92
5,098,997  3/1992  Anilionis et al. ........................ 530/350

OTHER PUBLICATIONS

Munson et al., J. Clin. Invest., vol. 72, 1983, pp. 677–684.

J.Clin.Invest, vol. 72, Aug. 1983, pp. 677–684, Robert S. Munson Jr. et al., "Purification and Comparison of Outer Membrane Protein P2 from Haemophilus Influenzae Type b Isolates".

*Primary Examiner*—Mindy Fleisher
*Assistant Examiner*—James Ketter
*Attorney, Agent, or Firm*—Sim & McBurney

[57] ABSTRACT

The nucleotide sequence of the P2 gene and the derived amino acid sequence of the P2 protein of *Haemophilus influenzae* type b are disclosed and the methods used to determine the same. Also disclosed are the methods used to clone and express the P2 gene as well as the purification protocol for the gene and protein. Also disclosed is the synthesis of peptides corresponding to the N-terminal and C-terminal ends of the P2 protein. Also disclosed is the use of the P2 protein as a protective agent for the disease caused by *Haemophilus influenzae* type b and the use of the protein as a carrier for conjugation with an oligosaccharide derived from Haemophilus to generate a potentially efficacious vaccine against the disease. Also disclosed is the use of P2 peptide-conjugates as immunising agents.

6 Claims, 9 Drawing Sheets

FIG.3

```
1H  ATGAAAAAACACTTGCAGCATTAATCGTTGGTGCATTCGCAGCTTCAGCAGCAAACGCA      60
    MetLysLysThrLeuAlaAlaLeuIleValGlyAlaPheAlaAlaSerAlaAlaAsnAla     -1

1H  GCTGTTGTTTATAACAACGAAGGACTAACGTAGAATTAGTGTGTCGTTTAAGCATTATC     120
    AlaValValTyrAsnAsnGluGlyThrAsnValGluLeuGlyGlyArgLeuSerIleIle     20
2L  ............................................................
6U  ............................................................

1H  GCAGAACAAAGTAATAGCACTGTAGATAATCAAAAACAGCAACACGGTGCATTACGCAAT    180
    AlaGluGlnSerAsnSerThrValAspAsnGlnLysGlnHisGlyAlaLeuArgAsn        40
2L  ............................................................
6U  ............................................................

1H  CAAGGTTCACGTTTCCACATTAAAGCAACTCATAACTTCGGTGATGGTTTCTATGCACAA    240
    GlnGlySerArgPheHisIleLysAlaThrHisAsnPheGlyAspGlyPheTyrAlaGln     60
2L  ............................................................
6U  ............................................................
```

FIG.3'

```
1H  GGTTATTAGAAACTCGTTTTGTTACAAAAGCCTCTGAAAACGGTTCAGATAACTTCGGT    300
    GlyTyrLeuGluThrArgPheValThrLysAlaSerGluAsnGlySerAspAsnPheGly    80
2L  ............................................................
6U  ............................................................

1H  GATATTACAAGCAAATATGCTTATGTTACTTTAGGAAATAAAGCATTCGGTGAAGTAAAA    360
    AspIleThrSerLysTyrAlaTyrValThrLeuGlyAsnLysAlaPheGlyGluValLys    100
2L  ............................................................
6U  .........................G..................................
                              Leu

1H  CTTGGTCGTGCGAAAACTATTGCTGATGGCCATAACAAGTGCAGAAGATAAAGAATATGGC    420
    LeuGlyArgAlaLysThrIleAlaAspGlyIleThrSerAlaGluAspLysGluTyrGly    120
2L  ............................................................
6U  ...........................C................................
```

FIG.3A

```
1H  GTTCTCAACAATAGTGACTATATTCCTACTAGTGGTAATACCGTTGGCTATACTTTAAA    480
    ValLeuAsnAsnSerAspTyrIleProThrSerGlyAsnThrValGlyTyrThrPheLys   140
2L  ............................................................
6U  ............................................................

1H  GGTATTGATGGTTTAGTATTATTAGGCGCTAATTATTTATTAGCACAAAAGCGTGAGGGTGCA   540
    GlyIleAspGlyLeuValLeuLeuGlyAlaAsnTyrLeuLeuAlaGlnLysArgGluGlyAla   160
2L  ................................................................
6U  ................................................................

1H  AAAGGTGAAAATAAGCGGCCTAATGATAAGGCTGGTGAAGTACGTATAGGTGAAATCAAT    600
    LysGlyGluAsnLysArgProAsnAspLysAlaGlyGluValArgIleGlyGluIleAsn   180
2L  ..........A.................A...............................
    ..........Gln...............................................
6U  ...ATG.C........T.........A.................................
    ...MetAla.......Leu.........Asn.............................
```

FIG.3A'

```
1H  AATGGAATTCAAGTTGGTGCAAATATGATGCAAACGACATCGTTGCAAAAATTGCTTAT    660
    AsnGlyIleGlnValGlyAlaGlyAlaAsnTyrAspAlaAsnAspIleValAlaAlaLysIleAlaTyr  200
2L  ................................................................
6U  ..........................A.....................................
                              Asn

1H  GGTAGAACTAACTACAAATATAACGAATCTGACGAGCATAAACAGCAATTAAATGGTGTA    720
    GlyArgThrAsnTyrLysTyrAsnGluSerAspGluHisLysGlnLeuAsnGlyVal     220
2L  ..........................G.....................................
                              Ala
6U  ...............................C................................
                                   Thr

1H  TTAGCAACTTTAGGCTATCGTTTTAGTGATTTAGGCTTATTAGTGTCTCTAGATAGTGGC   780
    LeuAlaThrLeuGlyTyrArgPheSerAspLeuGlyLeuLeuValSerLeuAspSerGly   240
2L  ................................................................
6U  ................................................................

1H  TATGCAAAAACTAAAACTATAAAATTAAACACGAAAAACGCTATTTCGTATCTCCAGGT    840
    TyrAlaLysThrLysAsnTyrLysIleLysHisGluLysArgTyrPheValSerProGly  260
2L  ..................................G.............................
                                       Val
6U  ................................................................
```

FIG.3B

```
1H  TTCCAATATGAATTAATGGAAGATACTAATGTCTATGGCAACTTCAAATATGAACGCACT  900
    PheGlnTyrGluLeuMetGluAspThrAsnValTyrGlyAsnPheLysTyrGluArgThr  280
2L  ............................................................
6U  ............................................................

1H  TCTGTAGATCAAGGTGAAAAACACGTGAACAAGCAGTATTATTCGGTGTAGATCATAAA   960
    SerValAspGlnGlyGluLysThrArgGluGlnAlaValLeuPheGlyValAspHisLys  300
2L  ............................................................
6U  ............................................................

1H  CTTCACAAACAACTATTAACCTATATATTGAAGGTGCTTACGCTAGAACAACTGAG     1020
    LeuHisLysGlnLeuLeuThrTyrIleGluGlyAlaTyrAlaArgThrThrGlu        320
2L  ............................................................
6U  ....................................................G.
                                                         Gly

1H  ACAGGTAAAGGCTAAAAACTGAAAAGAAAAATCAGTGGGTGTAGTTTACGCGTTTAC    1080
    ThrGlyLysGlyValLysGluLysThrGluLysSerValGlyLeuArgValTyr       340
2L  ............................................................
6U  ............................................................
```

FIG.3B'

```
1H  TTCTAATCATTTGTTAGAAATACATTATTAAAAGCAAGGCGAATCGAAAGATTCGCTTTT 1140
    Phe
2L        :     :     :     :     :
6U        :     :     :     :     :
```

FIG. 4

FIG. 5

MEMBRANE PROTEINS AND PEPTIDES OF HAEMOPHILUS INFLUENZAE TYPE B

This is a continuation of U.S. patent application Ser. No. 853,015 filed Mar. 18,1992, now abandoned, which itself is a continuation of application Ser. No. 456,000 filed Dec. 22, 1989 now abandoned.

FIELD OF INVENTION

The present invention relates to the DNA sequence of a protein obtained from *Haemophilus influenzae* type b and the modification of this sequence to give DNA, that, on expression in a suitable vector, gives proteins and peptides that retain all or some of the immunologic properties of the native protein. These proteins and peptides can be used, with or without conjugation, as vaccines against the disease of *Haemophilus influenzae* type b. The proteins also can be used with other haptens as a T-cell dependent antigen and carrier. The proteins and peptides also can be synthesized directly.

BACKGROUND OF THE INVENTION

The disease caused by *Haemophilus influenzae* type b is a major cause of bacterial meningitis in children under the age of five years. Protective antibodies to the disease are induced by the capsular polysaccharide of the organism and a vaccine has been developed that utilises the purified polyribosyl ribitol phosphate (PRP) as the antigen. This vaccine gave 90% protection in adults and in children over 24 months of age, but was ineffective in children under 24 months. Like other polysaccharide vaccines, PRP does not induce the proliferation of T-helper cells, and re-immunisation fails to elicit either a booster response or an increase in memory cells. A new conjugate vaccine has been developed that uses the PRP linked to diphtheria toxoid (see European Patent No. 0,098,581), which elicits T-cell dependent, booster responses and the production of PRP-specific IgG antibodies. However, the recommendation of both the Immunisation Practices Advisory Committee and the American Academy of Pediatrics is that only children 18 months and older should be immunised using the vaccine, since the efficacy of the vaccine was inconsistent at the younger ages. To achieve universal protection in the 2 to 6 month age group and certain high risk groups, the incorporation of certain non-capsular antigens may be required.

Methods for inducing immunity against disease are constantly improving and there is presently a move to use smaller and better defined materials as antigens. This is being undertaken to minimise or eliminate potential side-effects due to certain native immunogens, while preserving their immunogenicity to confer protection against the disease.

SUMMARY OF INVENTION

It has been shown that a protein isolated and purified from *Haemophilus influenzae* type b outer membrane and designated P2, will induce antibodies that are protective in rats against the disease. However, the structure of this protein was unknown heretofore. The inventors performed an N-terminal Edman degradation of the purified protein and from this sequence were able to synthesize an oligonucleotide probe to screen *Haemophilus influenzae* type b genomic libraries. This approach allowed the cloning of an approximately 1700 bp EcoRI fragment, which contained the 5' portion of the P2 gene. An overlapping PvuII fragment which contained the remainder of the P2 gene was subsequently cloned. The amino acid sequence of the P2 protein was obtained from the translation of the open reading frame of the DNA sequence for the overlapping fragments. The recombinant protein then was expressed in *E.coli*. The expressed protein was found to be immunologically similar to the one isolated from *Haemophilus influenzae* type b and thus could possibly be used as a protective agent against the disease. The inventors also have cloned and sequenced the same gene from other *Haemophilus influenzae* type b strains. These genes show minor polymorphism in both nucleotide and derived amino acid sequences.

Accordingly, in one aspect of the present invention, there is provided a gene coding for the outer membrane protein P2 from *Haemophilus influenzae* type b having the specific nucleotide sequence described herein or one substantially homologous thereto. The present invention also includes of genetically-engineered outer P2 membrane protein having the amino acid sequence described from the nucleotide sequence of the gene.

The inventors have further modified the gene by introducing a number of mutations to express a variety of protein analogues that retain all or some of the immunologic properties of the native protein. Some of these mutations are deletions resulting in proteins that are smaller than the original but still immunogenic.

Accordingly, in another aspect of the present invention, there is provided a gene which is a fragment or mutation of a gene having the specific nucleotide sequence described herein or substantially homologous thereto, and which, on expression in a suitable vector, provides a protein or peptide that possesses at least part of the immunological properties of a native protein of *Haemophilus influenzae* type b. In particular, the gene may be a modified P2 gene chromosomally reintegrated into *Haemophilus influenzae* type b genome. The present invention also includes a protein or peptide having at least part of the immunological properties of a native P2 protein of *Haemophilus influenzae* type b.

The protein or peptide may be a recombinant P2 protein or P2 protein fragment produced by a suitable expression system, such or *E.coli*, Bacillus, BCG, Yeast, Baculovirus, Adenovirus or mammalian expression systems. Alternatively, the protein or peptide may be produced synthetically. The immunologic proteins and peptides derived from the P2 amino acid sequence may form one component of a vaccine.

Because the P2 protein is a potentially protective antigen, it has been used by the inventors as part of a conjugate vaccine, wherein the hapten part of the conjugate is the capsular polysaccharide moiety of the Haemophilus organism. This avoids the problem of possible hyper-immunity to diphtheria when diphtheria toxoid is used as the conjugating protein (see European Patent No. 0,098,581), and ensures better protection against the disease, especially in infants.

In addition the inventors have synthesized two peptides with amino acid sequences corresponding to both N- and C-terminal regions of P2, using solid-phase peptide synthesis, that can act as antigens in a vaccine. These peptides can be used in a conjugate vaccine.

The present invention also provides biologically pure native P2 protein, extracted and purified from cultures of *Haemophilus influenzae* type b by a procedure involving dissolution of the protein in an aqueous urea solution.

BRIEF DESCRIPTION OF DRAWINGS

FIG. 4 shows the reconstruction of the P2 gene. The M13 phage containing the 1700 bp EcoRI fragment (mP2A) was subjected to oligonucleotide-directed mutagenesis to create an NdeI site at the translational initiation site. This phage was designated mP2Al. A replicative form of mP2Al was isolated, and the fragment of −600 bp containing the N-terminal portion of the P2 gene (hatched bars) was cloned into pT7-7 to create pRSM432. The −1 kbp EcoRI-PstI fragment containing the 3' portion of the P2 gene (solid bars) and approximately 500 bp 3' to the gene (open bars) was obtained from the replicative form of mP2B, the M13 phage containing the PvuII fragment, and cloned into pRSM432 to create pRSM478. Vector sequences are shown as lines. The position of the P2 gene and the direction of transcription from the T7010 promoter are shown by arrows.

GENERAL DESCRIPTION OF INVENTION

Figure 1:
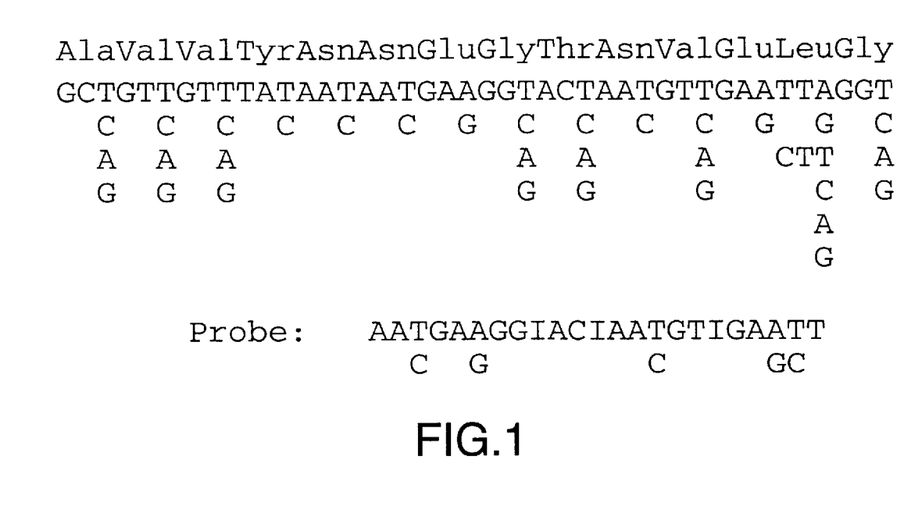
FIG. 1 shows the N-terminal amino acid sequence of the purified protein P2, the possible nucleotide sequences derived by reverse translation, and the oligonucleotide probe used to isolate the P2 gene.
Figure 2:
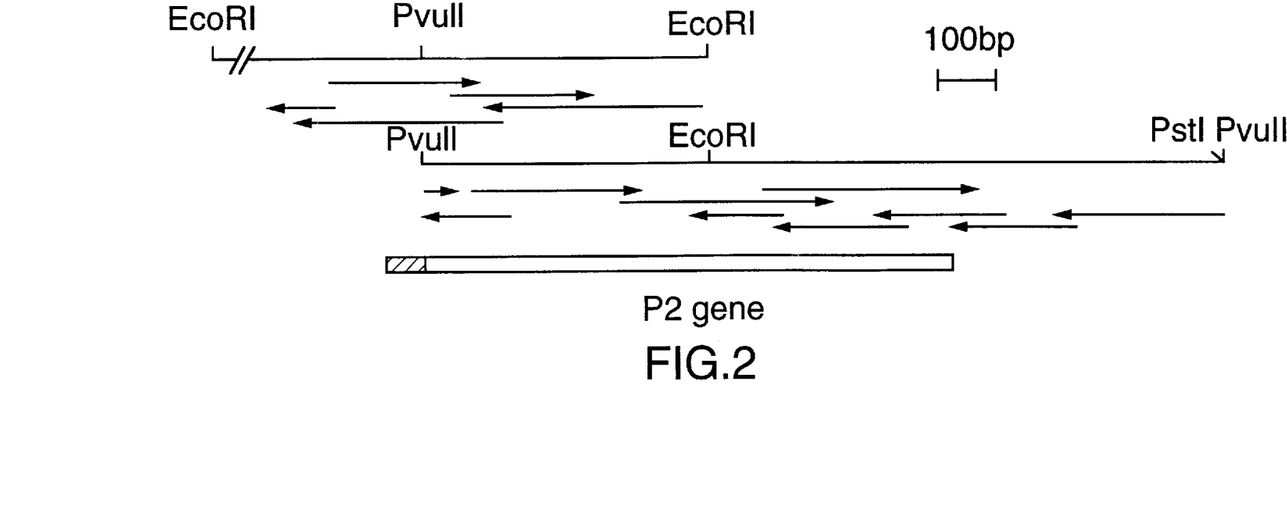
FIG. 2 shows the sequencing strategy used for the P2 gene. The EcoRI and PvuII fragments were cloned into M13 in both directions and sequenced by the dideoxy method with M13 primers and 20-mer oligonucleotide primers as indicated by the arrows. The coding region for the P2 gene is boxed; the open box represents the mature protein, and the solid box represents the signal peptide.
Figure 3:
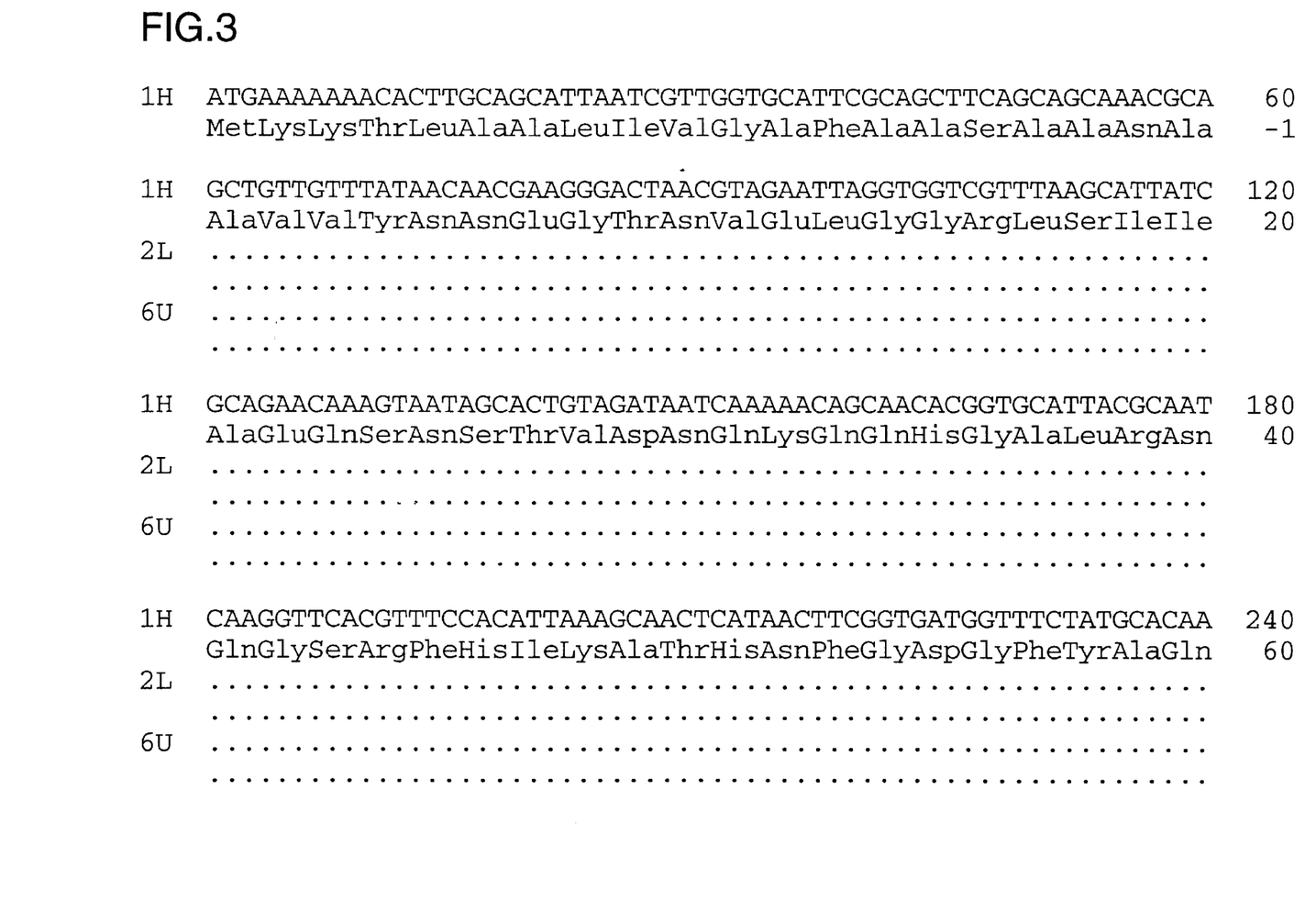
FIGS. 3', 3A, 3A', 3B and 3B' show the complete nucleotide and derived amino acid sequences of the P2 genes from strain Durst (OMP subtype 2L), strain 8358 (OMP subtype 6U) and strain MinnA (OMP subtype IH). The P2 gene from the OMP subtype 3L isolate is not shown since it is identical to the MinnA P2 gene.
Figure 3A:
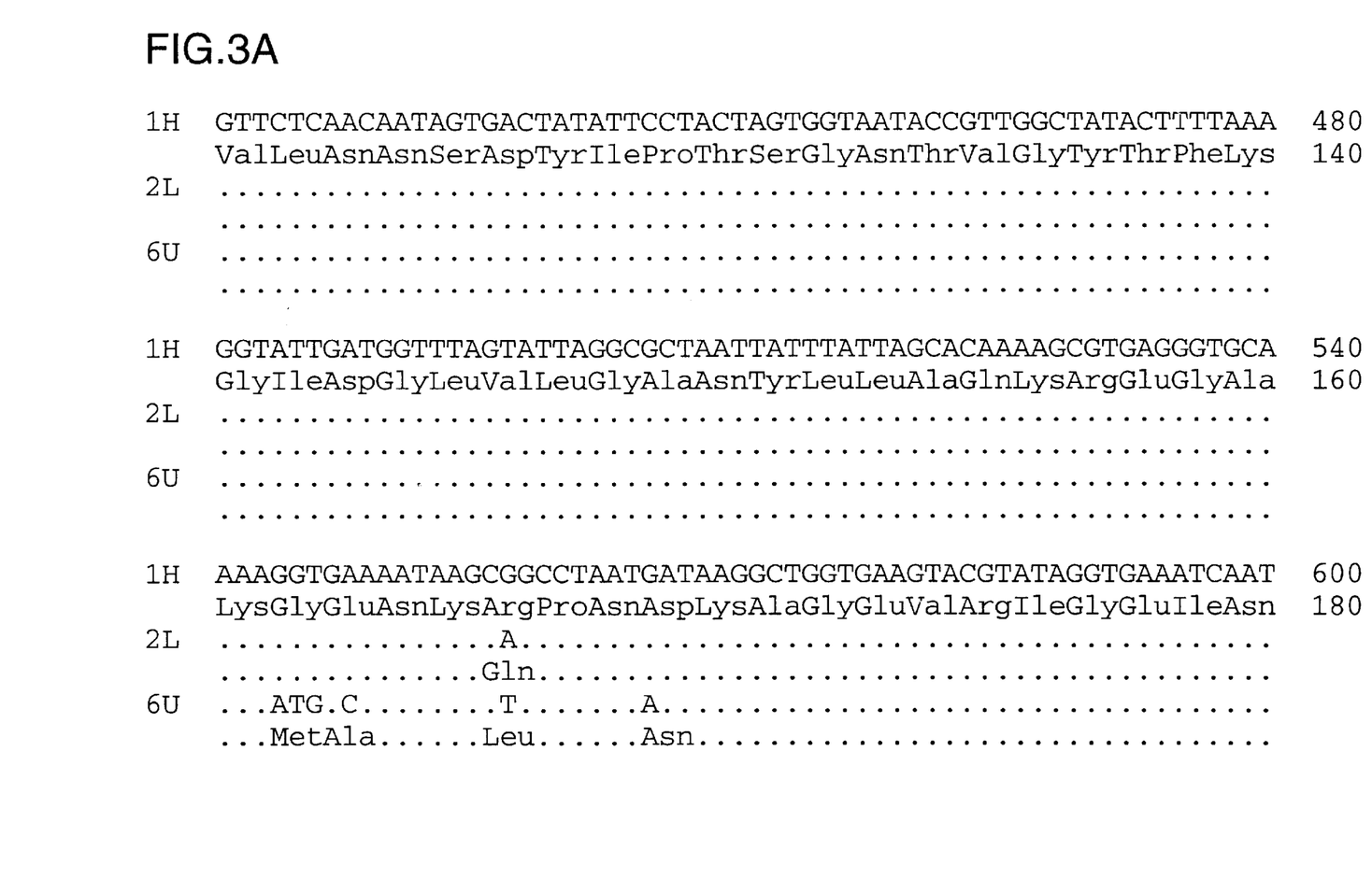
Figure 3B:
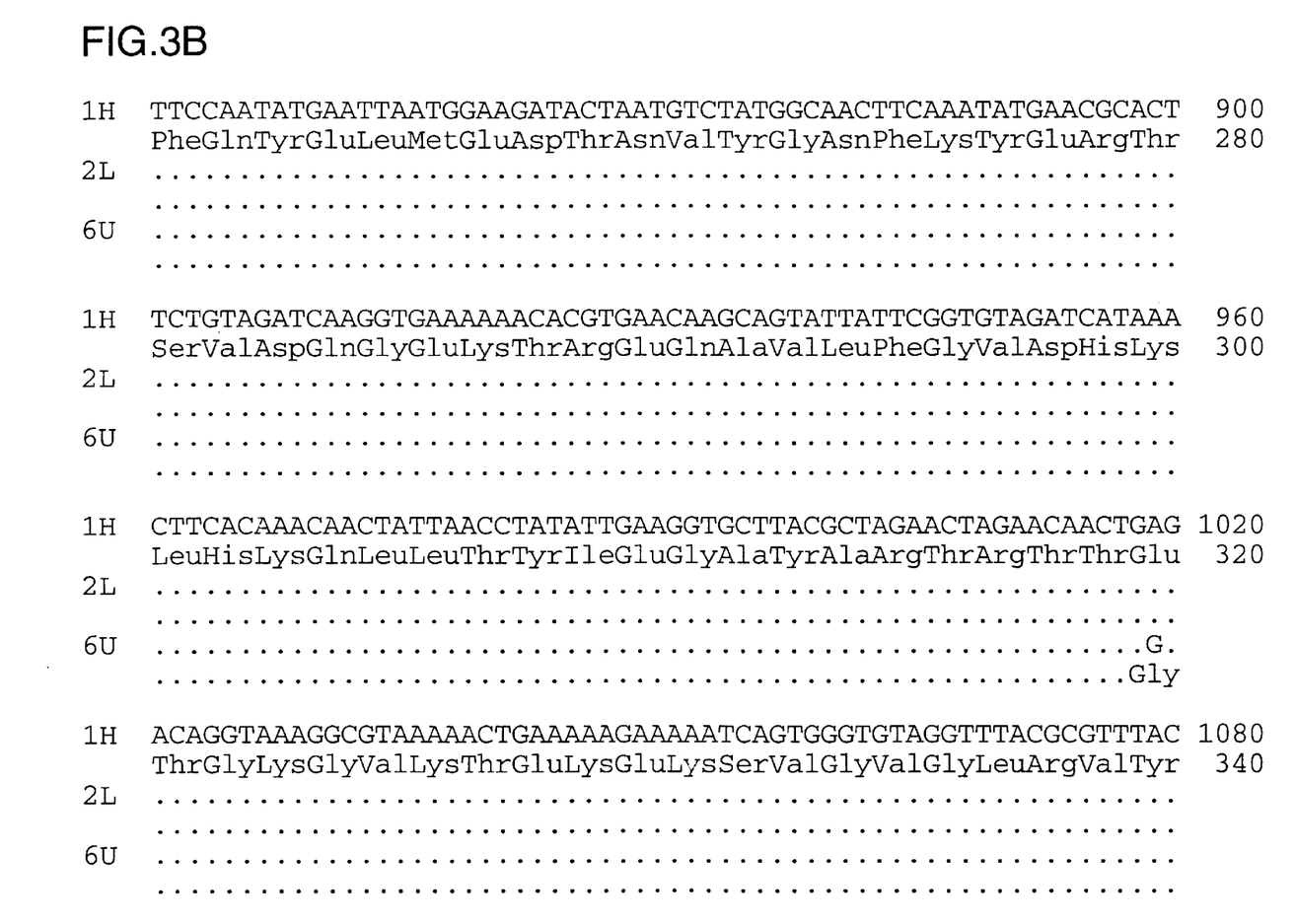

The gene coding for the outer membrane protein P2 from *Haemophilus influenzae* type b, strain MinnA, was cloned from a genomic library and its nucleotide sequence determined. Overlapping EcoRI and PvuII genomic fragments comprising the full sequence of the P2 gene were identified and clones screened by hybridisation to a mixed oligonucleotide probe (FIG. 1). The sequencing strategy is shown in FIG. 2. The complete nucleotide sequence of the P2 gene from strain MinnA and the derived amino acid sequence are shown in FIG. 3. The derived amino acid sequence was identical to portions of a sequence determined chemically, namely the N-terminal sequence and the sequence of an internal tryptic peptide. The amino acid composition of P2 derived from the P2 gene sequence was identical (within experimental error) to the chemically-determined amino acid analysis. Four subsequent clones, from other isolates, were isolated either as PvuII fragments or after polymerase chain reaction amplification of the P2 genes. The genes and derived amino acid sequences were found to be highly conserved. These nucleotide and derived amino acid sequences are compared to the corresponding sequences of strain MinnA (FIG. 3).

Figure 4:
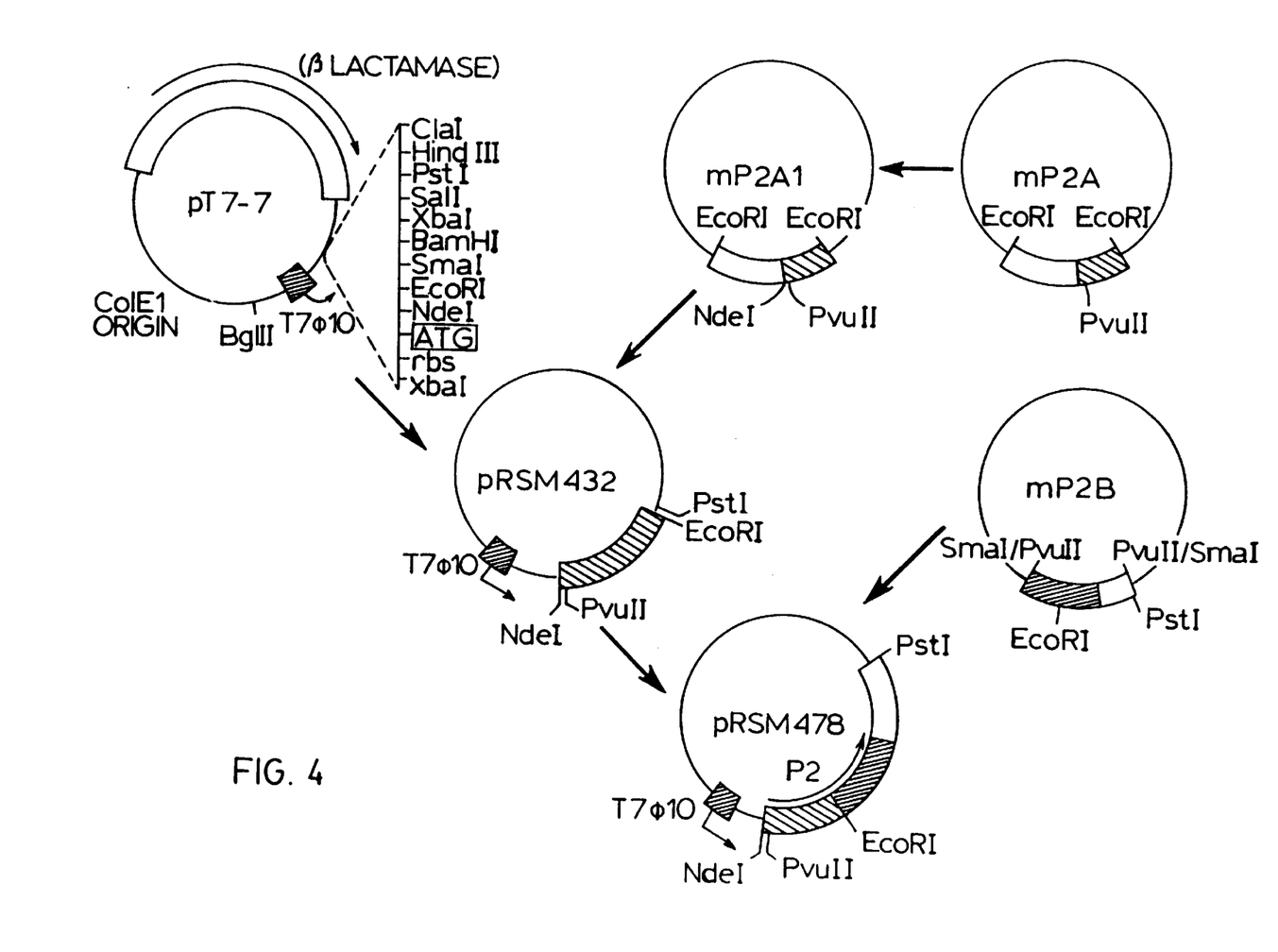

Reconstruction of the P2 gene was accomplished by religation of adjacent 5' and 3' restriction fragments. One example of the methodology is described in Example 2 below. In this Example, the entire P2 gene is reconstructed by site-directed mutagenesis of the 5'-restriction fragment to create an NdeI site at the translational start site, cloning of the NdeI-EcoRI fragment into the plasmid expression vector pT7-7, and subsequent cloning of the EcoRI to PstI fragment containing the 3' portion of the gene and downstream sequences immediately behind the NdeI to EcoRI fragment (FIG. 4). This construction was performed to a) remove the sequences 5' to the P2 gene translational start site and b) to place the P2 gene under the control of a regulatable promoter since unregulated expression of this gene in *E.coli* is lethal. The P2 gene from strain MinnA was expressed in *E.coli* and produced a gene product of the appropriate size. This gene product was recognised by rabbit antisera prepared against the P2 protein purified from Haemophilus.

One method to reduce the toxicity of P2 expression in *E.coli* is to remove the leader peptide coding sequence from the gene and express P2 either as a fusion protein or with a methionine preceding the mature protein sequence. Alternatively, fragments of the gene or truncated genes can be expressed either alone or as part of a fusion protein. Example III below demonstrates the construction of two such fusion proteins, one of which contains the coding sequences for the mature P2 protein with the exception of the N-terminal amino acid residue alanine. The second construct contains the coding sequence for the portion of the P2 gene 3' to the unique EcoRI restriction site. Both constructs are inserted into the pT7-7 vector and contain the transcriptional start site, the translational initiation codon and several amino acids encoded by DNA sequences from the multiple cloning region of the bacteriophage T7 protein 10 gene in pT7-7.

Antisera prepared against the partially purified recombinant fusion proteins reacted with the P2 protein produced in *Haemophilus influenzae* indicating that fusion proteins, and recombinant P2 fragments can induce antibodies which recognise native P2.

The gene, or fragments thereof, can be suitably expressed in *E.coli* under the control of other regulatable promoters, expressed in the absence of the leader peptide, or in other cloning systems where toxicity is not problematic. The gene or fragments thereof may be synthesized employing the polymerase chain reaction with suitable primers (see Example I below), or cloned in suitable cloning vectors or bacteriophage vectors in *E.coli* or other suitable hosts directly when toxicity can be avoided. Expression in gram-positive bacteria expression systems, vaccinia virus, adenovirus, baculovirus, yeast, fungi, BCG or mammalian expression systems may be suitable alternative expression systems.

Haemophilus oligosaccharides (HPRP) prepared by controlled acid hydrolysis were conjugated with purified P2 protein using cyanogen bromide activation. The mean molecular size of the PRP molecule used for conjugation was determined as being approximately 20,000 Daltons. No linker molecule was used in the conjugation. A PRP/protein ratio of approximately seven was used to provide an excess of the hapten. Analysis of the product after reaction showed the ratio of PRP/protein to be about 0.1. The conjugate was tested for immunogenicity in rabbits and primary and secondary anti-PRP immune responses were observed (Table 1 below). Also rabbit anti-PRP-P2 antisera showed a strong reaction against P2 in immunoblot analysis. This data indicates that P2 can be used as a carrier protein in a conjugate vaccine thus avoiding the problem of possible hyperimmunity to diphtheria or tetanus when diphtheria or tetanus toxoids are used as the conjugation protein. In addition, PRP-P2 as a vaccine would possibly ensure a more consistent protection against *Haemophilus influenzae* type b disease, particularly in infants, as a result of homotypic protection provided by antibodies to the P2 protein.

Since P2 has been shown to have porin activity and antibodies against P2 are protective in the rat bacteremic model, the inventors decided to identify the protective epitope(s) of P2 and to generate probes to localise and characterise the P2 functional domains to be incorporated into a P2-based *Haemophilus influenzae* type b vaccine. Both N- and C-terminal sequences were predicted to be hydrophilic in the Kyte-Doolittle plot of the P2 protein sequence and were thus chosen to be studied first. Porin-I (residues 1–14) and C-HIBP2 (residues 314–341) peptides were chemically synthesized with an additional cysteine at the C-terminal end and the N-terminal end, respectively. The unique cysteine at one end of the peptide allows its coupling to the carrier protein in one specific orientation. It was found that the bifunctional cross-linker, Sulfo-SIAB, was a better reagent than m-maleimidobenzoyl-N-hydroxysuccinimide ester (MBS) for coupling cysteine-containing peptides to a protein carrier.

Both synthetic peptides, Porin-1 and C-HIBP2, were assessed for their reactivity with antisera raised against native P2 in mice and guinea pigs in a peptide-specific ELISAs. All of the anti-P2 antisera recognised the C-HIBP2 peptide very well but did not react with Porin-1 in the assay. This data indicates that a major immunodominant B-cell epitope of P2 is located within the C-terminal region (residues 314–341).

To determine whether the synthetic peptides were possible vaccine candidates, peptide-KLH conjugates were assessed individually for their immunogenicity. Rabbits were immunised and the anti-peptide antisera tested by ELISA, double immunodiffusion and immunoblot techniques. The rabbit antisera were shown to be monospecific for their respective immunising peptides by ELISA. Both porin-1 and C-HIBP2 specific antibodies recognised P2 in all assays used, which indicates that both terminal regions are exposed and free to interact with antibodies. Since both peptide-KLH conjugates induced a strong antibody response in rabbits, it is obvious that they can act as antigens in a vaccine preparation.

EXAMPLES

Methods of molecular genetics, protein biochemistry and hybridoma technology used but not explicitly described in this disclosure and these Examples are amply reported in the scientific literature and are well within the ability of those skilled in the art.

Example I

This Example illustrates the cloning and sequencing of the P2 gene.

Chromosomal DNA was obtained from *Haemophilus influenzae* type b isolates by standard methods, digested to completion with EcoRI, PvuII, PstI or a combination of PstI and PvuII. Two ug of digested DNA were applied to each lane of a 0.7% agarose gel, electrophoresed and transferred to Hybond-N membranes according to the manufacturer's instructions. A mixed oligonucleotide probe was synthesized, based on N-terminal sequence data, and end labelled with [$-^{32}$P]ATP. A single EcoRI fragment of approximately 1700 base pairs, a unique PvuII fragment of approximately 1600 base pairs and a unique PstI fragment of approximately 10,000 base pairs hybridised to this probe.

Chromosomal DNA was digested with EcoRI and 1000–2000 base pair fragments were isolated, cloned into the vector λ gt11. *E.coli* was infected with the recombinant λ gt11 clones and plaques were screened by hybridisation. A clone containing the approximately 1700 base pair EcoRI fragment was isolated and characterised. The EcoRI fragment was moved to a bacteriophage M13 vector and partially sequenced. Dideoxy sequencing was performed, employing the mixed oligonucleotide probe as a primer. Additional primers were generated and the 5' end of the P2 gene was sequenced as shown in FIG. 2. A unique PvuII site was identified near the 3' end of the DNA sequence coding for the leader peptide. As noted above, the genomic PvuII fragment which contained the P2 gene was approximately 1600 base pairs in size. A partial library of PvuII fragments was generated in M13, clones identified by hybridisation and sequenced as shown in FIG. 2.

P2 genes from other *Haemophilus influenzae* type b isolates were cloned as PvuII restriction fragments, or after amplification of genomic DNA by polymerase chain reaction. The oligonucleotides employed for the amplification were the following:

5' CTTGGATCCTTAATCGTTGGTGCATTCGCAGC and
5' GCAAAGCTTGCGAATCTTTCGATTCGCCT.

These oligonucleotides contain unique restriction sites at their 5' ends to facilitate cloning after polymerase chain reaction amplification of the gene. The cloned PvuII genomic fragments, or the genes cloned after amplification, were fully sequenced.

Example II

This Example illustrates the reconstruction and expression of the P2 gene in *E.coli*.

Figure 5:
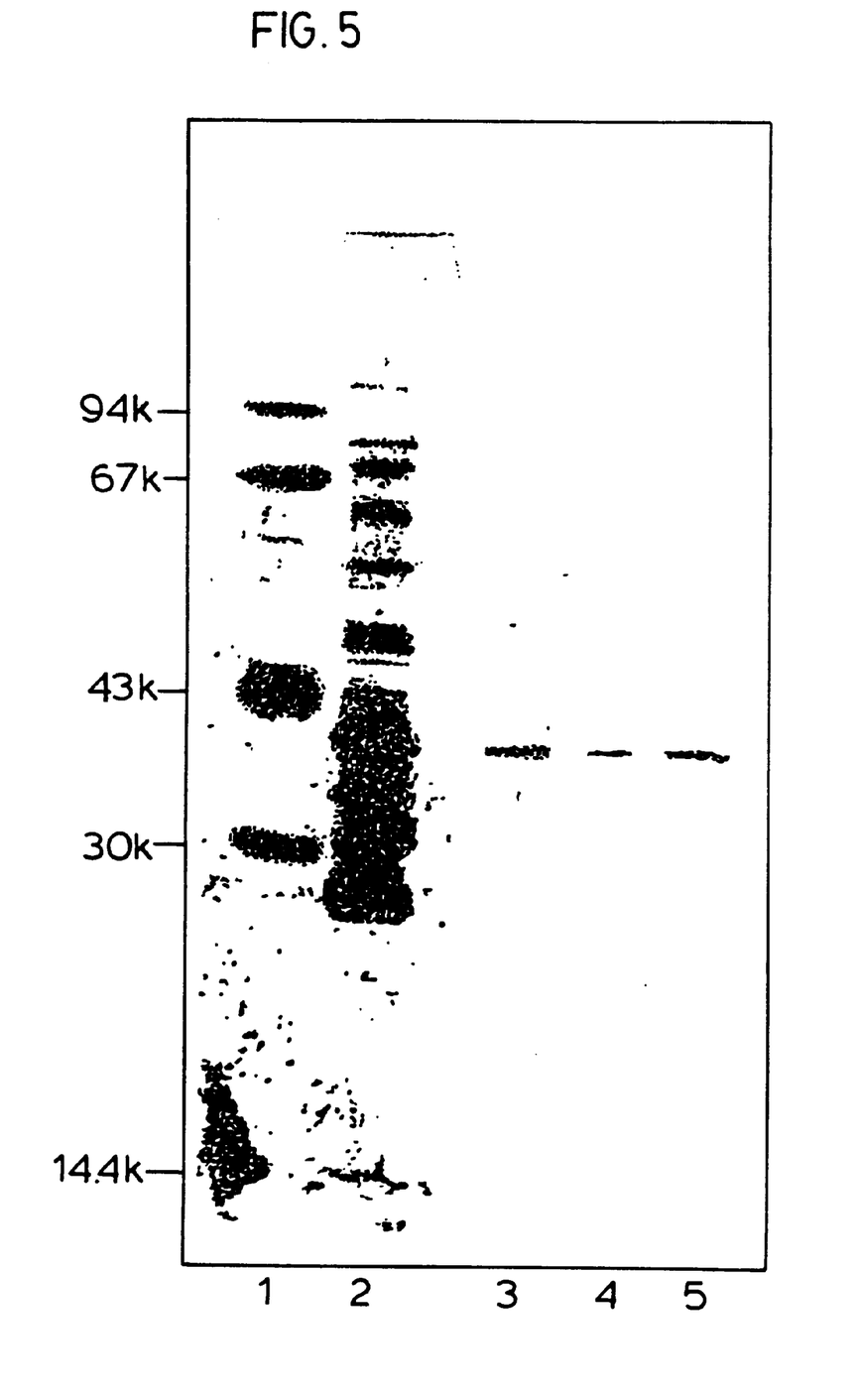
FIG. 5 shows a Western blot analysis of JM101 (pRSM478). Lane 1 contains molecular weight markers. Lane 2 contains a detergent insoluble fraction enriched in outer membrane proteins from H.influenzae type b MinnA. Lanes 3 to 5 contain sonicates from the following strains and were developed with an anti-P2 antiserum; H.influenzae type b MinnA (lane 3); JMIOl(pRSM478) uninduced (lane 4); JMlOl(pRSM478) induced with mGPl-2 (lane 5).

Sequences 5' to the structural P2 gene were removed and the P2 gene was reconstructed downstream from the regulatable bacteriophage T7 promoter in the vector pT7-7. Site-directed mutagenesis was performed on a clone containing the approximately 1700 base pair EcoRI fragment in order to generate an NdeI site at the translation initiation site of the P2 gene. The NdeI to EcoRI fragment was then sub-cloned from the replicative form of the M13 recombinant into pT7-7. The remainder of the gene was then added as the EcoRI-PstI fragment as shown in FIG. 4. The construct was transformed into *E.coli* strain JMIO1. Recombinant P2 (rP2) of the appropriate size was detected in extracts of this strain as determined by the Western blot technique using an anti-native P2 antiserum (FIG. 5). Infection of this strain with a bacteriophage expressing the bacteriophage T7 RNA polymerase gene under the control of the lac promoter/operator (in the presence of isopropylthiogalactoside) led to increased levels of rP2 synthesis.

Example III

This Example illustrates the construction of genes resulting in fusion proteins which express P2 epitopes.

The PvuII to PstI fragment containing the DNA sequence coding for most of the mature P2 protein and the EcoRI to PstI fragment containing the coding sequences of the 3' portion of the P2 gene were cloned into the pT7-7 vector which had been cleaved with SmaI and PstI or EcoRI and PstI, respectively. In-frame fusions with the bacteriophage T7 gene 10 protein were created in these clones. The constructs were transformed into a derivative of the *E.coli* strain BL21 which was lysogenic for the phage DE3. DE3 contains the T7 RNA polymerase gene under the control of the lac operator/promoter. T7 RNA polymerase was induced by the addition of isopropylthiogalactoside. The fusion protein genes were then transcribed and translated. The fusion proteins accumulated in insoluble inclusion bodies and were partially purified by pelleting over 2M sucrose after cell lysis by sonication. Mice were immunised with the partially purified fusion proteins. These antisera recognised P2 produced by *Haemophilus influenzae*.

Example IV

This Example illustrates the purification of protein P2 from *Haemophilus influenzae* type b cultures.

Native P2 protein was purified from Cetavlon (0.1%) precipitates of the Eagen strain fermentation culture. Culture paste was homogenized for 90 sec. in a polytron in the presence of 4M urea/phosphate buffered saline (PBS), and the suspension was allowed to stir for 90 min. at room temperature. Centrifugation at 8,000 g for 30 min. yielded a clear supernatant, which was subjected to dialysis against PBS, to remove urea. During dialysis a heavy precipitate was formed, which was collected by centrifugation at 8,000 g for 30 min. The precipitate was then suspended in a buffer containing 2% Octylglucoside/0.2% sodium deoxycholate/ 100 mM Tris, pH 8. At this stage the P2 preparation was >95% pure as judged by SDS PAGE analysis.

Example V

This Example illustrates the preparation of the oligosaccharide/P2 conjugate.

Purified polysaccharide (PRP) from *Haemophilus influenzae* type b (U.S. Pat. No. 4,496,538) was heated to 80–90° C. in 0.1M sodium citrate at pH 3.2 for sufficient time to achieve a molecular size range of 15–40,000 Daltons as determined by gel filtration on a Sephacryl S-200 column.

A volume of the PRP was diluted to 25 mg/mL in 0.85% sodium chloride and 6.7% triethylamine hydrochloride at pH 8.5. With stirring in an ice bath, a total of 0.1 volume of a concentrated solution of cyanogen bromide (1 g dissolved in 1mL acetone) was added in 5 equal aliquots, spaced one minute apart. Between additions, the pH was maintained between 8.0 and 9.0 by the addition of 1.0N sodium hydroxide solution. Two minutes after the final addition, the pH of the reaction mixture was reduced to 6.0 with 1.0N hydrochloric acid. The activated polysaccharide was purified by diafiltration against 0.85% sodium chloride at 4° C. to remove low molecular weight reactants. The PRP concentration was maintained at 25 mg/mL.

Purified P2 protein was concentrated to approximately 3.5 mg/mL by ultrafiltration at 4° C. and then diafiltered at 4° C. against 0.85% sodium chloride containing 1.0% octylglucoside to remove Tris and deoxycholate. Equal volumes of diafiltered purified P2 protein and diafiltered, activated PRP were mixed together in a vessel that could be sealed. The pH was adjusted to 8.5 and the reaction mixture tumbled for 15–18 hours at 4° C. No attempt was made at this point to purify the conjugate away from unreacted protein or PRP.

The polysaccharide and protein concentrations in the mixtures were determined by standard tests.

Example VI

This Example illustrates the synthesis of peptides and the preparation of peptide carriers.

Peptides corresponding to the N- and C-terminal sequences of P2, respectively, were synthesized in a commercial peptide synthesizer, and subsequently cleaved from the resin using hydrofluoric acid and purified by reverse-phase HPLC using a Vydac C4 column and a linear acetonitrile gradient (0–40%) in 0.1% trifluoracetic acid. Peptide Porin-1 contains the N-terminal sequence (residues 1–14) and an additional cysteine. Its sequence is Ala-Val-Val-Tyr-Asn-Asn-Glu-Gly-Thr-Asn-Val-Glu-Gly-Cys. Peptide C-HIBP2 contains the C-terminal sequence (residues 314–341) and an additional cysteine. Its sequence is Cys-Ala-Arg-Thr-Arg-Thr-Thr-Glu-Thr-Gly-Lys-Gly-Val-Lys-Thr-Glu-Lys-Glu-Lys-Ser-Val-Gly-Val-Gly-Leu-Arg-Val-Tyr-Phe. All synthetic peptides used for immunogenicity studies were >95% pure as judged by HPLC analysis. The amino acid analyses of the peptide hydrolysates were in good agreement with the theoretical compositions.

Individual peptides were conjugated to KLH (keyhole limpet haemocyanin) or BSA (bovine serum albumin) at a 10:1 molar ratio of peptide over carrier protein by a standard method (Liu et al., Biochemistry, 18, 690, (1979)) with the following modification. The carrier protein was first modified with sulphosuccinimyl(4-iodoacetyl)-aminobenzoate (Sulfo-SIAB). The modified protein was further purified by gel filtration HPLC. The peptide was subsequently mixed with the modified protein carrier for 4–6 hrs, and the peptide-carrier conjugate isolated gel filtration.

Example VII

This Example illustrates the protocols used to immunise animals and prepare antisera.

P2 protein-specific and peptide-specific antisera were prepared as follows. Rabbits, guinea pigs or mice were immunised intramuscularly with P2, PRP-P2 or individual peptide-KLH conjugates emulsified in complete Freund's adjuvant. Between 20 and 500 ug of the materials in 500 uL of phosphate-buffered saline (PBS) were used for each injection. Blood was collected from the animals every two weeks after the first injection. Sera were separated from the clotted blood samples by centrifugation and heat inactivated at 56° C. for 30 minutes, then stored at −20° C.

Example VIII

This Example illustrates the preparation of an ELISA specific for P2 peptides.

Individual P2 peptides (5 ug/well) were directly coated onto microtitre plates by incubation for 16 hrs. at 4° C. The wells were then blocked with 3% bovine serum albumin (BSA) in PBS for 30 min. Serially diluted rabbit, guinea pig or mouse P2-specific to peptide-specific antisera were added to the wells and the plates incubated for 2 hrs. at room temperature. Excess antibody was removed by washing 3 times with wash buffer (0.1% Tween 20 in PBS). A commercial Protein A-peroxidase conjugate was added to each well and the plates were further incubated at room temperature for 1 hr. After removal of the excess Protein A-peroxidase conjugate, the plates were washed 4 times with wash buffer and 0.2 mL of tetramethylbenzidine (TMB) substrate was added to each well. The plates were incubated in the dark until colour developed. The reaction was stopped by the addition of 50 uL of 1N sulphuric acid and the wells read in an ELISA reader at 450 nm.

Example IX

This Example illustrates the use of the immunoblotting technique to characterise anti-P2 antisera.

Antibodies prepared in rabbits against the native protein P2, recombinant P2, synthetic KLH-peptide conjugates and PRP-P2 conjugates were tested for their specificity using the immunoblotting technique. Purified native P2 and recombinant P2 were electrophoresed and subsequently electrotransferred from an SDS-PAGE gel to a nitrocellulose strip, as described in the literature (Towbin et al., Proc. Nat. Acad. Sci., 76, 4350 (1979)). The nitrocellulose strips then were incubated for 2–4 hrs with appropriate dilutions of various rabbit antisera raised against native P2, recombinant P2, synthetic KLH-peptide conjugates or PRP- P2 conjugates. The antisera were diluted 1:500 with wash buffer (phosphate buffered saline containing 0.1% Triton X-100). Excess antibody was removed by washing 3–5 times with the wash buffer. Goat anti-rabbit IgG antibody conjugated to alkaline-phosphatase was purchased from a commercial source and used as the second antibody according to the manufacturer's instructions.

SUMMARY OF DISCLOSURE

In summary of this disclosure, the present invention provides the nucleotide sequence of the P2 gene and the derived amino acid sequence of the P2 protein of *Haemophilus influence* type b, includes methods to clone and express the P2 gene as well as its purification protocol and peptides corresponding to the N-terminal and C-terminal ends of the P2 protein are included, includes the use of the P2 protein as a protection agent for the disease caused by H.flu b and as a carrier for conjugation with an oligosaccharide derived from Haemophilus to generate as potentially efficacious vaccine against the disease, and includes the use of P2 peptide-conjugates as immunising agents. Modifications are possible within the scope of this invention.

TABLE 1

HUMORAL RESPONSES OF RABBITS IMMUNISED WITH DIFFERENT TYPES OF PRP-PROTEIN CONJUGATES*

| Immunogen | Lot # | Preimmune | Titre of rabbit antibodies against PRP (ELISA units)** | | |
|---|---|---|---|---|---|
| | | | Post 1 | Post 2 | Post 3 |
| poPRP-M-CRM | 114A-85-1A | 35 | 981 | 8342 | 4345 |
| poPRP-M-CRM | 114A-85-2A | 44 | 642 | 1510 | 289 |
| HPRP-P2 | 114A-91 | 46 | 2230 | 9328 | 6840 |
| HPRP-D | 4672 | 30 | 45 | 286 | 2083 |

*The Experimental detail should be referred to Examples VI & VIII.
**Determined by conventional PRP-specific ELISA

What we claim is:

1. A method for forming an immunogenic composition, comprising:
   providing an expression vector containing an entire DNA sequence shown contiguously in FIG. 3, 3A and 3B encoding an entire P2 outer membrane protein of a strain of *Haemophilus influenzae* type b under control of a promoter,
   transforming the expression vector into a bacterial strain,
   expressing the entire P2 outer membrane protein encoded by said DNA sequence to produce a recombinantly expressed P2 outer membrane protein from a *Haemophilus influenzae* type b strain having an entire derived amino acid sequence of FIG. 3,
   isolating and purifying the recombinantly expressed P2 outer membrane protein,
   conjugating the isolated and purified P2 outer membrane protein to a capsular polysaccharide moiety of a Haemophilus organism which is a PRP of *Haemophilus influenzae* type b to form a conjugate molecule, and
   formulating the conjugate molecule as an immunogenic composition.

2. A conjugate molecule, consisting of a synthetic peptide having an amino acid sequence which is either the N-terminal amino acid residues 1 to 14 or the C-terminal amino acid residues 314 to 341 of the P2 outer membrane protein of a strain of *Haemophilus influenzae* type b having the derived amino acid sequence shown contiguously in FIG. 3, 3A and 3B and a carrier protein for said synthetic peptide.

3. A method for forming a conjugate molecule, comprising:
   providing an expression vector containing an entire DNA sequence shown contiguously in FIG. 3, 3A and 3B encoding an entire P2 outer membrane protein of a strain of *Haemophilus influenzae* type b under control of a promoter,
   transforming the expression vector into a bacterial strain,
   expressing the P2 outer membrane protein encoded by said DNA sequence to produce a recombinantly expressed P2 outer membrane protein from a strain of *Haemophilus influenzae* type b having an entire derived amino acid sequence of FIG. 3, and
   conjugating the P2 outer membrane protein to a capsular polysaccharide moiety of a Haemophilus organism which is a PRP of *Haemophilus influenzae* type b.

4. The method of claim 3 wherein said *Haemophilus influenzae* type b is selected from the group consisting of MinnA, Durst, OMP subtype 6U and OMP subtype 3L strains.

5. The method of claim 1 wherein said PRP of *Haemophilus influenzae* type b has been heat treated to attain a molecular size of 15,000 to 40,000 daltons.

6. The method of claim 3 wherein said PRP of *Haemophilus influenzae* type b has been heat treated to attain a molecular size of 15,000 to 40,000 daltons.

* * * * *